(12) United States Patent
Mizutani et al.

(10) Patent No.: US 7,771,576 B2
(45) Date of Patent: Aug. 10, 2010

(54) GAS SENSOR AND METHOD FOR MANUFACTURING GAS SENSOR

(75) Inventors: Masaki Mizutani, Aichi (JP); Shigeki Mori, Seki (JP); Shigeo Kondo, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 306 days.

(21) Appl. No.: 11/779,074

(22) Filed: Jul. 17, 2007

(65) Prior Publication Data

US 2008/0016947 A1 Jan. 24, 2008

(30) Foreign Application Priority Data

Jul. 18, 2006 (JP) .......................... P 2006-195783

(51) Int. Cl.
 *G01N 27/26* (2006.01)
 *G01N 7/08* (2006.01)
(52) U.S. Cl. ..................... 204/424; 73/23.31
(58) Field of Classification Search ............... 73/23.31, 73/23.32; 204/424, 425, 426, 427, 428, 429
See application file for complete search history.

(56) References Cited

U.S. PATENT DOCUMENTS

| | | | | |
|---|---|---|---|---|
| 4,292,158 A | * | 9/1981 | Muller et al. | 204/429 |
| 6,375,816 B1 | * | 4/2002 | Jach et al. | 204/425 |
| 6,695,964 B1 | * | 2/2004 | Ando et al. | 205/781 |
| 6,866,517 B2 | * | 3/2005 | Kimata et al. | 439/33 |
| 6,923,902 B2 | * | 8/2005 | Ando et al. | 205/781 |
| 7,462,266 B2 | * | 12/2008 | Miyata et al. | 204/408 |
| 7,497,933 B2 | * | 3/2009 | Kurachi et al. | 204/427 |
| 7,501,604 B2 | * | 3/2009 | Diehl | 219/494 |
| 2004/0129564 A1 | * | 7/2004 | Kurachi et al. | 204/424 |
| 2007/0108049 A1 | * | 5/2007 | Wahl et al. | 204/424 |
| 2010/0000293 A1 | * | 1/2010 | Kawai et al. | 73/31.05 |

FOREIGN PATENT DOCUMENTS

| | | |
|---|---|---|
| JP | 61-134655 A | 6/1986 |
| JP | 2001-242129 A | 9/2001 |
| JP | 2001-311714 A | 11/2001 |
| JP | 2002-107335 A | 4/2002 |

* cited by examiner

*Primary Examiner*—Lisa M Caputo
*Assistant Examiner*—Punam Roy
(74) *Attorney, Agent, or Firm*—Sughrue Mion, PLLC

(57) ABSTRACT

A gas sensor including a plate-like gas detecting element which extends in a longitudinal direction and in which a plurality of ceramic layers are stacked and a detecting portion is provided at a leading end side of the gas detecting element, the gas detecting element including: a first ceramic layer; a second ceramic layer; a bottom ceramic layer; a first through-hole conductor; a first connecting layer; a second through-hole conductor; and a second connecting layer, as defined herein.

14 Claims, 9 Drawing Sheets

GAS SENSOR AND METHOD FOR MANUFACTURING GAS SENSOR

BACKGROUND OF THE INVENTION

1. Field of the Invention

The present invention relates to a gas sensor having a stacked-type gas detecting element in which a plurality of ceramic layers are stacked, as well as a method for manufacturing the same.

2. Description of the Related Art

Conventionally, a plate-like gas detecting element is known which extends in a longitudinal direction. A plurality of ceramic layers are stacked to form the plate-like gas detecting element, and a detecting portion is formed at a leading end side thereof. Such gas detecting elements are disclosed, for example, in JP-A-61-134655, JP-A-2001-242129, JP-A-2001-311714 and JP-A-2002-107335. Through holes penetrating the ceramic layers are provided in the gas detecting element. In each of these through holes, a conductor is provided for electrically connecting a lead portion extending from a sensing electrode disposed in the interior of the gas detecting element and an electrode pad disposed on an outer surface of the gas detecting element.

3. Problems to be Solved by the Invention

The present inventors invented a gas detecting element 900 shown in FIG. 9. Specifically, a solid electrolyte layer 913 has a first through hole 913$h$ penetrating between the first surface 913$a$ and the second surface 913$b$ of the solid electrolyte layer 913, and the second surface 913$b$ side of the first through hole 913$h$ is closed by a first insulating layer 911. A first through-hole conductor 921 is formed on the inner peripheral surface of the first through hole 913$h$ so as to connect a first connecting layer 923 formed on the first surface 913$a$ of the solid electrolyte layer 913 and a lead portion 931 formed on the second surface 913$b$ of the solid electrolyte layer 913.

In addition, a second through hole 915$h$ is formed in a second insulating layer 915, and a second through-hole conductor 925 is formed on a portion (left side in FIG. 9) of the inner peripheral surface of this second through hole 915$h$. Further, a second connecting layer 927, which is connected to the second through-hole conductor 925 and is overlappingly connected to the first connecting layer 923, is formed on the first connecting layer 923. Furthermore, a filled through-hole conductor 929, which is connected to the second connecting layer 927, is filled and formed in the first through hole 913$h$ (on the inner side of the first through-hole conductor 921) of the solid electrolyte layer 913.

Such a gas detecting element 900 can be formed as follows: Namely, an unsintered solid electrolyte layer is prepared which forms the solid electrolyte layer 913 after sintering. Then, a first unsintered through-hole conductor, which forms the first through-hole conductor 921 after sintering, is formed on the inner peripheral surface of its first through hole by printing a conductor paste. In addition, a first unsintered connecting layer, which forms the first connecting layer 923 after sintering, is formed on the first surface of this unsintered solid electrolyte layer, and an unsintered lead portion, which forms the lead portion 931 after sintering, is formed on the second surface of this unsintered solid electrolyte layer.

Subsequently, the unsintered solid electrolyte layer is stacked on the first unsintered insulating layer which forms the first insulating layer 911 after sintering. Furthermore, a second unsintered insulating layer, which forms the second insulating layer 915 after sintering, is formed on this stacked body.

Next, a second unsintered through-hole conductor which forms the second through-hole conductor 925 after sintering, a second unsintered connecting layer which forms the second connecting layer 927 after sintering, and an unsintered filled through-hole conductor which forms the filled through-hole conductor 929 after sintering, are formed by printing the conductor paste.

Then, upon sintering, the stacked body of the unsintered ceramic, the gas detecting element 900 is formed.

However, with such a gas detecting element 900, there are cases where a crack occurs in the filled through-hole conductor 929 itself or at a connecting layer between the filled through-hole conductor 929 and the other conductor 931 during sintering. Conceivably, the reason is that since the amount of shrinkage upon sintering differs among the unsintered solid electrolyte layer, the unsintered insulating layer (first unsintered insulating layer) and the unsintered conductor, a large stress is applied to the filled through-hole conductor 929 having a relatively large volume and to a connecting layer between the same and the other conductor 931. If such a crack occurs, the electrical connection reliability may suffer.

SUMMARY OF THE INVENTION

The present invention has been made in view of the above-described circumstances, and an object thereof is to provide a gas sensor having a gas detecting element which is capable of improving the reliability of both electrical connection of conductors and between the conductor and other conductors formed in the interior of the element, as well as a method for manufacturing the gas sensor.

The above object has been achieved, in accordance with a first aspect of the invention, by providing a gas sensor comprising a gas detecting element extending in a longitudinal direction and in which a plurality of ceramic layers are stacked, and wherein a detecting portion is provided at a leading end side thereof, the gas detecting element comprising: a first ceramic layer having a first surface and a second surface and having a first through hole penetrating therethrough (i.e., penetrating between the first surface and the second surface); a second ceramic layer stacked on a side of the first surface of the first ceramic layer and having a second through hole connected to the first through hole, the second through hole having an opening area larger than the first through hole; a bottom ceramic layer stacked on a side of the second surface of the first ceramic layer to close one end of the first through hole; a first through-hole conductor formed on an inner peripheral surface of the first through hole; a first connecting layer provided on the first surface of the first ceramic layer and connected to the first through-hole conductor; a second through-hole conductor formed on an inner peripheral surface of the second through hole; and a second connecting layer having one end disposed on the first connecting layer and another end connected to the second through-hole conductor.

According to the above-described first aspect of the invention, the gas detecting element has a first through-hole conductor formed on an inner peripheral surface of the first through hole and a second through-hole conductor formed on an inner peripheral surface of the second through hole. The first connecting layer formed on the first surface of the first ceramic layer is connected to the first through-hole conductor. In addition, the other end of the second connecting layer having one end disposed on the first connecting layer is connected to the second through-hole conductor.

In the above-described gas detecting element, the first through-hole conductor and the second through-hole conductor are reliably connected through the first connecting layer and the second connecting layer which are connected in a mutually overlapping manner. Consequently, reliability of electrical connection is high as compared with the case where the first and second connecting layers are absent. Further, in this gas detecting element, since the second connecting layer is not present inside the first through hole, i.e., since a portion corresponding to the filled through-hole conductor 929 shown in FIG. 9 is not present, cracks hardly occur in the conductor itself or in a connecting layer between a conductor and other conductors during sintering or during operation of the gas sensor. Accordingly, the reliability of both electrical connection of the conductor itself and between a conductor and other conductors is high, so that the resulting gas detecting element and gas sensor can achieve greater reliability.

It should be noted that the "gas sensor" of the invention encompasses, for example, an oxygen sensor, an air-fuel ratio sensor, an $NO_x$ sensor, a $CO_2$ sensor, and the like, so long as the above-described requirements are satisfied.

The "gas detecting element" encompasses a plurality of stacked ceramic layers, and the gas detecting element may have a pair of electrodes or a plurality of pairs of electrodes. In addition, the "gas detecting element" includes one in which a heater or the like is formed integrally therewith.

The "first through-hole conductor" and the "second through-hole conductor" are formed on inner peripheral surfaces of the first through hole and the second through hole, respectively. For example, the first through-hole conductor and the second through-hole conductor may be cylindrical in shape and formed on the entire inner peripheral surfaces of the first through hole and the second through hole. In addition, these through-hole conductors may be, for instance, U-shaped in cross section and formed only on portions of the inner peripheral surfaces of the first through hole and the second through hole.

The "first connecting layer" is connected to the first through-hole conductor and is provided on the first surface of the first ceramic layer, and its shape is not particularly limited. Similarly, the "second connecting layer" has one end connected to the first connecting layer and another end connected to the second through-hole conductor, and its shape is not particularly limited. Further, the "first connecting layer" and the "second connecting layer" overlap one another on the inner side of the second through hole and are electrically connected. The first connecting layer and the second connecting layer may be connected in their entireties, or the first connecting layer and the second connecting layer may be connected only at partial portions thereof.

Furthermore, according to another aspect of the invention, in the above-described gas sensor, a first surface of the bottom ceramic layer may be exposed in the first through hole.

In a case where a conductor is present on the bottom surface of the first through hole, there is a possibility that, owing to the effect of this conductor, a crack may occur in the conductor itself or a connecting layer between the conductor and other conductors during sintering.

By contrast, in the invention, since the first surface of the bottom ceramic layer is exposed, i.e., since the conductor is not present on the bottom surface of the first through hole, there is no possibility of such a problem occurring. Accordingly, the reliability of both electrical connection of the conductor itself and between a conductor and other conductors is higher, so that the resulting gas detecting element and the gas sensor can achieve greater reliability.

According to yet another aspect of the invention, in the above-described gas sensor, a relationship D1>D2>0 is satisfied, where D1 represents a longitudinal distance between a leading end of the first through hole and a leading end of the second through hole, and D2 represents a longitudinal distance between a base end of the first through hole and a base end of the second through hole.

The first through hole is ordinarily provided on the base end side of the gas detecting element. By providing a structure such that D1>D2, as described above, the longitudinal distance between the base end of the gas detecting element and the second through hole can be made larger, and the first through hole can be set closer to the base end of the gas detecting element.

According to yet another aspect of the invention, the above-described gas sensor may further comprise: an electrode pad electrically connected to the second through-hole conductor and provided on an outer surface of the gas detecting element; and a connection terminal abutting the electrode pad so as to be electrically connected to the electrode pad, wherein the second through hole and a position of abutment between the connection terminal and the electrode pad are offset in the longitudinal direction.

Since the position of abutment between the connection terminal and the electrode pad is thus offset from the second through hole in the longitudinal direction, even if the connection terminal firmly presses the electrode pad to establish electrical conduction, since the second through hole is not formed at that abutment position, breakage and the like of the gas detecting element are unlikely to occur.

According to yet a further aspect of the invention, in the above-described gas sensor, a thickness of the second ceramic layer may be smaller than a thickness of the first ceramic layer.

Since the relatively large second through hole is thus formed in the second ceramic layer, the mechanical strength of the gas detecting element at its portion where the second through hole is formed is reduced. However, by making the thickness of the second ceramic layer relatively small, it is possible to suppress deterioration in mechanical strength. The thickness of the second ceramic layer is preferably set to be not more than half the thickness of the first ceramic layer.

According to a further aspect of the invention, in the above-described gas sensor, the gas detecting element may further comprise: a third ceramic layer having a first surface and a second surface and having a third through hole penetrating therethrough; a third through-hole conductor formed on an inner peripheral surface of the third through hole; and a third connecting layer provided on the second surface of the third ceramic layer and connecting the third through-hole conductor and the second through-hole conductor, wherein the second ceramic layer is stacked on the side of the second surface of the third ceramic layer, and the second through hole is connected to the third through hole and has an opening area larger than that of the third through hole.

As the opening area of the second through hole is thus made larger than that of the third through hole, the third connecting layer can be formed on the second surface of the third ceramic layer within the second through hole. Accordingly, the reliability of electrical connection of the conductor itself is high, so that the resulting gas detecting element and gas sensor can achieve greater reliability.

In addition, according to a further aspect of the invention for attaining the above-described object, a method is provided for manufacturing a gas sensor including a gas detecting element extending in a longitudinal direction and in which a plurality of ceramic layers are stacked, and wherein a detecting portion is formed at a leading end side thereof, said method comprising: in a first ceramic green sheet having a first surface and a second surface and having a first through hole penetrating therethrough (i.e., penetrating between the first surface and the second surface), forming a first unsintered through-hole conductor on an inner peripheral surface of the first through hole and forming on the first surface a first unsintered connecting layer for connecting to the first unsintered through-hole conductor; stacking a bottom ceramic green sheet on a side of the second surface of the first ceramic green sheet so as to close an end of the first throughhole; stacking on a side of the first surface of the first ceramic green sheet a second unsintered ceramic layer having a second through hole formed in a position corresponding to the first through hole, the second through hole having a cross-sectional area larger than that of the first through hole; printing a conductor paste on an inner peripheral surface of the second through hole and the first surface of the first ceramic sheet exposed in the second through hole, to thereby form a second unsintered through-hole conductor provided on the inner peripheral surface of the second through hole and a second unsintered connecting layer having one end connected to the second unsintered through-hole conductor and another end formed on the first connecting layer; and sintering a completed stacked body.

Since the amount of sintering shrinkage differs between an unsintered ceramic and an unsintered conductor, as described above, with the gas detecting element 900 shown in FIG. 9, there are cases where cracks occur in the filled through-hole conductor 929 itself or at a connecting layer between the filled through-hole conductor 929 and another conductor 931 during sintering. Consequently, the reliability of electrical connection between the conductors may decrease.

To cope with such a problem, in the invention, not only the first unsintered through-hole conductor but also the first unsintered connecting layer which is connected thereto are formed on the first ceramic green sheet. In addition, not only the second unsintered through-hole conductor but also the second unsintered connecting layer which is connected thereto are formed on the second ceramic layer. Then, sintering is effected in a state in which the second unsintered connecting layer overlaps the first unsintered connecting layer, to thereby form a gas detecting element having the first and second through-hole conductors and the first and second connecting layers. If the gas detecting element is formed in this manner, the first through-hole conductor and the second through-hole conductor can be connected reliably by means of the first and second connecting layers.

Furthermore, in the invention, when the second unsintered through-hole conductor and the second unsintered connecting layer are formed, the other end of the second unsintered connecting layer is disposed on the first unsintered connecting layer. Namely, an unsintered through-hole conductor which is formed into the filled through-hole conductor 929 shown in FIG. 9 after sintering is not present. For this reason, it is possible to prevent or suppress the occurrence of cracks in the conductor itself or a connecting layer between the conductor and other conductors during sintering. Accordingly, the reliability of both electrical connection of the conductor itself and between a conductor and other conductors can be enhanced, and therefore it is possible to manufacture a gas detecting element and gas sensor of greater reliability.

It should be noted that, in the third step, the second unsintered ceramic layer can be formed, for instance, by printing an insulation paste, as described below. In addition, the second unsintered ceramic layer can also be formed by stacking a ceramic green sheet which is prepared separately in advance.

According to a further aspect of the invention, in the above-described method for manufacturing a gas sensor, a surface of the bottom ceramic green sheet (at a portion closing the first through hole) is exposed in the first through hole.

In a case where a conductor is present on the bottom ceramic green sheet within the first through hole, there is a possibility that, due to the effect of this conductor, a crack may occur in the conductor itself or in a connecting layer between the conductor and other conductors during sintering.

By contrast, in the invention, since the bottom ceramic green sheet within the first through hole is exposed, there is no possibility of such a problem occurring. Accordingly, the reliability of both electrical connection of the conductor itself and between a conductor and other conductors can be enhanced, so that it is possible to manufacture a gas detecting element and a gas sensor of greater reliability.

According to a further aspect of the invention, in the above-described method for manufacturing a gas sensor, a relationship D3>D4>0 is satisfied, where D3 represents a longitudinal distance between a leading end of the first through hole and a leading end of the second through hole, and D4 represents a longitudinal distance between a base end of the first through hole and a base end of the fourth through hole.

The first through hole is ordinarily provided on the base end side of the gas detecting element. By providing a structure such that D3>D4, as described above, the longitudinal distance between the base end of the gas detecting element and the second through hole can be made larger, and the first through hole can be set closer to the base end of the gas detecting element. More specifically, the distance between the first through hole and the base end of the gas detecting element can be set to not greater than 3 mm.

According to a further aspect of the invention, in the above-described method for manufacturing a gas sensor, a thickness of the second unsintered ceramic layer is smaller than a thickness of the first ceramic green sheet.

The second through hole having a relatively large cross-sectional area is formed in the second unsintered ceramic layer, and can possibly lead to a decline in mechanical strength of the unsintered stacked body. By contrast, by making the thickness of the second unsintered ceramic layer relatively small, it is possible to suppress a decline in mechanical strength of the unsintered stacked body.

According to yet a further aspect of the invention, in the above-described method for manufacturing a gas sensor, the second unsintered ceramic layer may be formed by printing an insulation paste.

In the case where the second unsintered ceramic layer is formed by stacking a ceramic green sheet, it is also possible to adopt a method in which the second unsintered through-hole conductor and the second unsintered connecting layer are formed in advance by printing on that ceramic green sheet, and this ceramic green sheet is subsequently stacked. By so doing, the bottom ceramic green can be exposed in the first through hole, so that it is possible to prevent or suppress the occurrence of cracks in the conductor and the like during sintering.

By contrast, in the invention, by adopting a method such that the second unsintered ceramic layer is formed by printing an insulation paste, the second unsintered through-hole conductor and the second unsintered connecting layer cannot be formed in advance by printing on the second unsintered ceramic layer. However, even in such a case, by adopting the invention, the ceramic green sheet can be easily formed so as to be exposed in the first through hole. Accordingly, it is possible to prevent or suppress the occurrence of cracks in the conductor itself or a connecting layer between the conductor and other conductors during sintering.

According to a further aspect of the invention, in the above-described method for manufacturing a gas sensor, the second unsintered ceramic layer is formed to have a thickness of not greater than 100 μm.

In the case where a thin second unsintered ceramic layer having a thickness of not greater than 100 μm is formed, it is difficult for the reason of sheet handling and the like to adopt the method for forming the second unsintered ceramic layer by stacking a ceramic green sheet as described above. For this reason, the second unsintered ceramic layer is formed by printing an insulation paste, so that the second unsintered through-hole conductor and the second unsintered connecting layer cannot be formed in advance by printing on the second unsintered ceramic layer. However, as described above, even in such a case, by adopting the invention, the ceramic green sheet can be easily formed so as to be exposed in the first through hole. Accordingly, it is possible to prevent or suppress the occurrence of cracks in the conductor itself or in a connecting layer between the conductor and other conductors during sintering.

In addition, according to a further aspect of the invention for attaining the above-described object, a gas sensor is provided comprising a gas detecting element extending in a longitudinal direction and in which a plurality of ceramic layers are stacked, and wherein a detecting portion is provided at a leading end side thereof, the gas detecting element comprising: a first ceramic layer having a first surface and a second surface; a third ceramic layer having a first surface and a second surface and having a third through hole penetrating therethrough (i.e., penetrating between the first surface and the second surface); a second ceramic layer provided between the first surface of the first ceramic layer and the second surface of the third ceramic layer and having a second through hole connected to the third through hole, the second through hole having an opening area larger than that of the third through hole; a first connecting layer provided on the first surface of the first ceramic layer and exposed in the second through hole; a second through-hole conductor provided on an inner peripheral surface of the second through hole; a second connecting layer having one end disposed on the first connecting layer and another end connected to the second through-hole conductor; a third through-hole conductor provided on an inner peripheral surface of the third through hole; and a third connecting layer provided on the second surface of the third ceramic layer and connecting the second through-hole conductor and the third through-hole conductor.

As the opening area of the second through hole is thus made larger than that of the third through hole, the second through-hole conductor and the third through-hole conductor are connected with each other through the third connecting layer formed on the second surface of the third ceramic layer within the second through hole. Accordingly, the reliability of both electrical connection of the conductor itself and between the first connecting layer and the conductor are enhanced, so that the resulting gas detecting element and gas sensor can achieve higher reliability.

According to a further aspect of the invention, in the above-described gas sensor, the gas detecting element may further comprise: an electrode pad electrically connected to the second through-hole conductor and provided on an outer surface of the gas detecting element; and a connection terminal abutting the electrode pad at a position located closer to a longitudinal base end side than the third through hole so as to be electrically connected to the electrode pad, and wherein a relationship D5>D6>0 is satisfied, where D5 represents a longitudinal distance between a leading end of the second through hole and a leading end of the third through hole, and D6 represents a longitudinal distance between a base end of the second through hole and a base end of the third through hole.

In a form in which the connection terminal abuts the connection pad at a position closer to the longitudinal base end side than the second through hole, by enlarging the length of the through hole on the leading end side, the second through hole and the position of connection between the connection terminal and the connection pad can be easily offset from one another in the longitudinal direction. Accordingly, it is possible to increase the connection reliability between the connection terminal and the connection pad and the mechanical strength of the sensor detecting element.

DESCRIPTION OF REFERENCE NUMERALS

Figure 1:
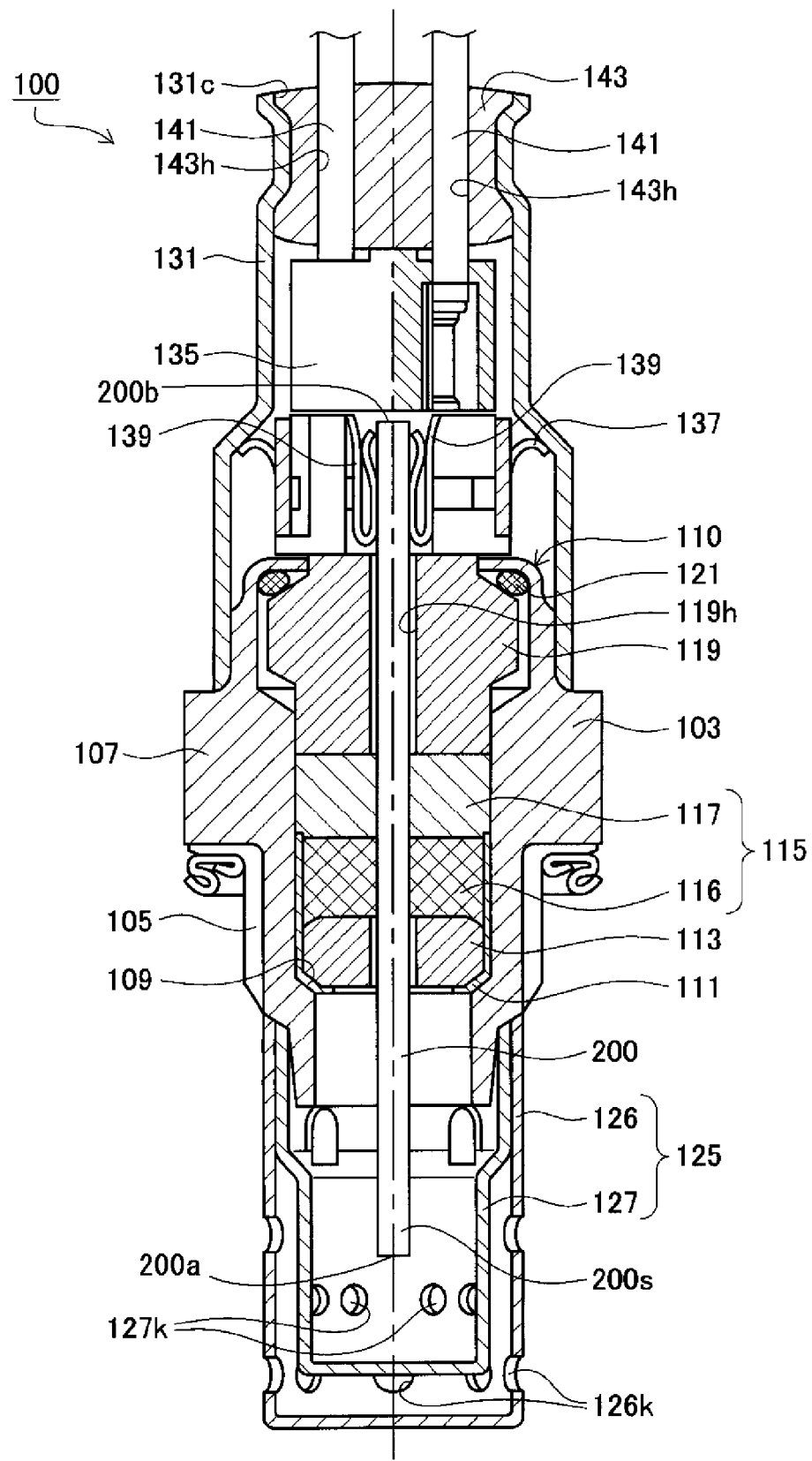
FIG. 1 is a longitudinal cross-sectional view of an oxygen sensor in accordance with an embodiment of the invention.

Reference numerals used to identify various structural features in the drawings include the following.
100: oxygen sensor (gas sensor)
200: gas detecting element
200*a*: leading end of the gas detecting element
200*b*: base end of the gas detecting element
201: sensor portion
211: first solid electrolyte layer (first ceramic layer)
211*h*: first through hole
213: first electrode
215: second electrode
217: first through-hole conductor
213*c*, 219: first connecting layer
221: second solid electrolyte layer (third ceramic layer)
221*h*1, 221*h*2: third through hole
223: third electrode
224, 225*c*: third connecting layer
225: fourth electrode
231: insulating layer (second ceramic layer)
231*h*1, 231*h*2: second through hole 233d, 235d: second through-hole conductor
233f, 235f: second connecting layer
241: protective layer (fourth ceramic layer)
241h1, 241h2, 241h3: fourth through hole
253: first heater ceramic layer (bottom ceramic layer)
255: second heater ceramic layer
929: filled through-hole conductor

DETAILED DESCRIPTION OF THE INVENTION

A preferred embodiment of the present invention will now be described in greater detail by reference to the drawings. However, the present invention should not be construed as being limited thereto.

FIG. 1 shows an oxygen sensor (gas sensor) 100 in accordance with this embodiment. The oxygen sensor 100 is mounted on an exhaust pipe (not shown) of an automobile to detect the oxygen concentration in exhaust gas. In FIG. 1, the lower side of the oxygen sensor 100 is designated a leading end side, and the upper side thereof is designated a base end side. This oxygen sensor 100 comprises a gas detecting element 200, a cylindrical metal shell 103 for holding the gas detecting element 200 in its interior, a protector 125 fitted to a predetermined portion on the leading end side of this metal shell 103, a cylindrical casing 131 connected to a predetermined portion on the base end side of this metal shell 103, among other structural elements.

Figure 2:
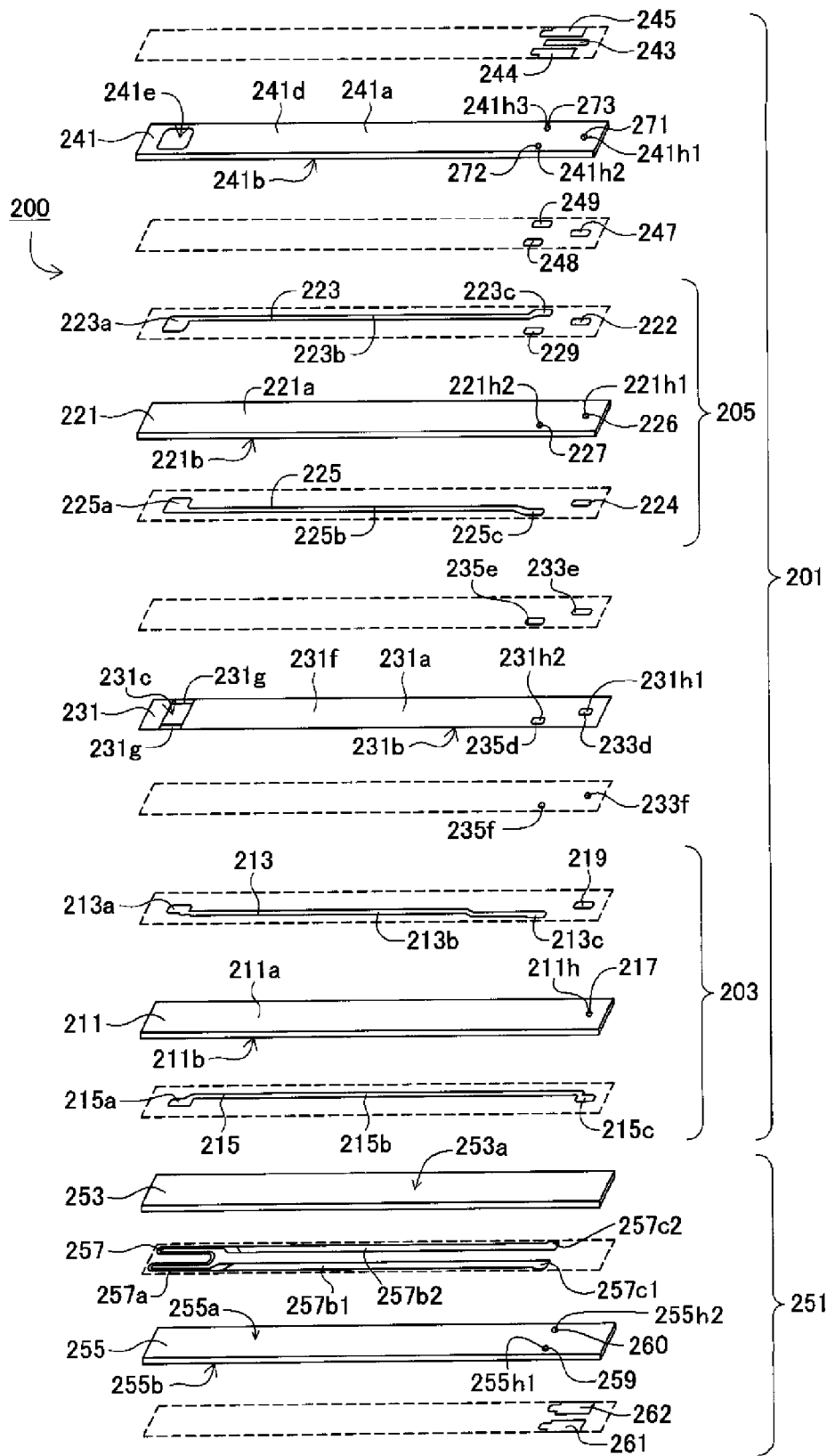
FIG. 2 is an exploded perspective view of a gas detecting element in accordance with the embodiment.

Of these, the gas detecting element 200 has a leading end 200a and a base end 200b, and is a rectangular plate-shaped stacked-type element in which a plurality of ceramic layers are stacked, its size being approx. 50 mm long, approx. 4 mm wide, and approx. 1.2 mm thick. As shown in the exploded perspective view of FIG. 2, the gas detecting element 200, when classified into its major components, includes a sensor portion 201 capable of sensing the oxygen concentration and a heater portion 251 capable of heating the sensor portion 201. In FIG. 2, the left side of the gas detecting element 200 is designated the leading end 200a side, and the right side thereof is designated the base end (rear end) 200b side.

The sensor portion 201 has an oxygen concentration detection cell 203, an oxygen pump cell 205, and a protection layer 241.

The oxygen concentration detection cell 203 has a first solid electrolyte layer (first ceramic layer) 211 composed of a sintered compact of partially stabilized zirconia, a first electrode 213 formed on a first surface 211a of the first solid electrolyte layer 211, and a second electrode 215 formed on a second surface 211b thereof.

The first electrode 213 includes of a first electrode portion 213a disposed on the leading end side, an elliptical first connecting layer 213c extending in a longitudinal direction, and a lead portion 213b connecting the first electrode portion 213a and the first connecting layer 213c. The first electrode 213 is formed of platinum.

Similarly, the second electrode 215 includes of a second electrode portion 215a disposed at a position opposing the first electrode portion 213a, an elliptical connecting layer 215c extending in the longitudinal direction, and a lead portion 215b connecting the second electrode portion 215a and the connecting layer 215c. This second electrode 215 is also formed of platinum.

In addition, a first through hole 211h penetrating between the first surface 211a and the second surface 211b is provided on the base end side of the first solid electrolyte layer 211. Further, a first through-hole conductor 217 is formed on the inner peripheral surface of this first through hole 211h so as to connect a first connecting layer 219 provided on the first surface 211a of the first solid electrolyte layer 211 and the connecting layer 215c provided on the second surface 211b thereof. It should be noted that this first through hole 211h is closed by a first heater ceramic layer (bottom ceramic layer) 253 stacked on the second surface 211b side. Meanwhile, unlike the gas detecting element 900 shown in FIG. 9, a conductor corresponding to the filled through-hole conductor 929 is absent on a bottom surface 211ht of the through hole 211h (see FIG. 3).

Next, a description will be given of the oxygen pump cell 205 (see FIG. 2). The oxygen pump cell 205 comprises a second solid electrolyte layer (third ceramic layer) 221 composed of a sintered compact of partially stabilized zirconia, a third electrode 223 formed on a first surface 221a of the second solid electrolyte layer 221, and a fourth electrode 225 formed on a second surface 221b of the second solid electrolyte layer 221.

The third electrode 223 includes of a third electrode portion 223a disposed on the leading end side, an elliptical connecting layer 223c disposed on the base end side and extending in the longitudinal direction, and a lead portion 223b connecting the third electrode portion 223a and the connecting layer 223c. The third electrode 223 is also formed of platinum.

The fourth electrode 225 includes of a fourth electrode portion 225a disposed at a position opposing the third electrode portion 223a, an elliptical third connecting layer 225c disposed on the base end side and extending in the longitudinal direction, and a lead portion 225b connecting the fourth electrode portion 225a and the third connecting layer 225c. The fourth electrode 225 is also formed of platinum.

In addition, the second solid electrolyte layer 221 has a first surface 221a and a second surface 221b, and two third through holes 221h1 and 221h2 are provided on its base end side. A third through-hole conductor 226 is formed on an inner peripheral surface of the third through hole 221h1 so as to connect a connecting layer 222 formed on the first surface 221a and a third connecting layer 224 formed on the second surface 221b (see FIG. 3). In addition, a third through-hole conductor 227 is formed on an inner peripheral surface of the third through hole 221h2 so as to connect a connecting layer 229 formed on the first surface 221a and the third connecting layer 225c formed on the second surface 221b (see FIG. 4).

Returning to FIG. 2, an insulating layer (second ceramic layer) 231 whose main constituent is alumina is disposed between the oxygen concentration detection cell 203 and the oxygen pump cell 205 mentioned above. This insulating layer 231 includes an insulating portion 231f which occupies a major portion of the insulating layer 231 and a pair of porous diffusion rate controlling portions 231g disposed at predetermined positions on the leading end side. A gas measurement chamber 231c having a rectangular shape in plan view is formed in the insulating layer 231 at a position corresponding to both the first electrode portion 213a of the oxygen concentration detection cell 203 and the fourth electrode portion 225a of the oxygen pump cell 205. This gas measurement chamber 231c communicates with the outside through the aforementioned pair of diffusion rate controlling portions 231g at both widthwise end portions of the insulating layer 231. In this manner, the diffusion rate controlling portions 231g are able to control the diffusion rate therethrough at the time when the detection gas flows into the gas measurement chamber 231c.

In addition, second through holes 231h1 and 231h2, which have an elliptical shape extending in the longitudinal direction, are formed on the base end side of the insulating layer 231 so as to penetrate between a first surface 231a and a second surface 231b.

Figure 3:
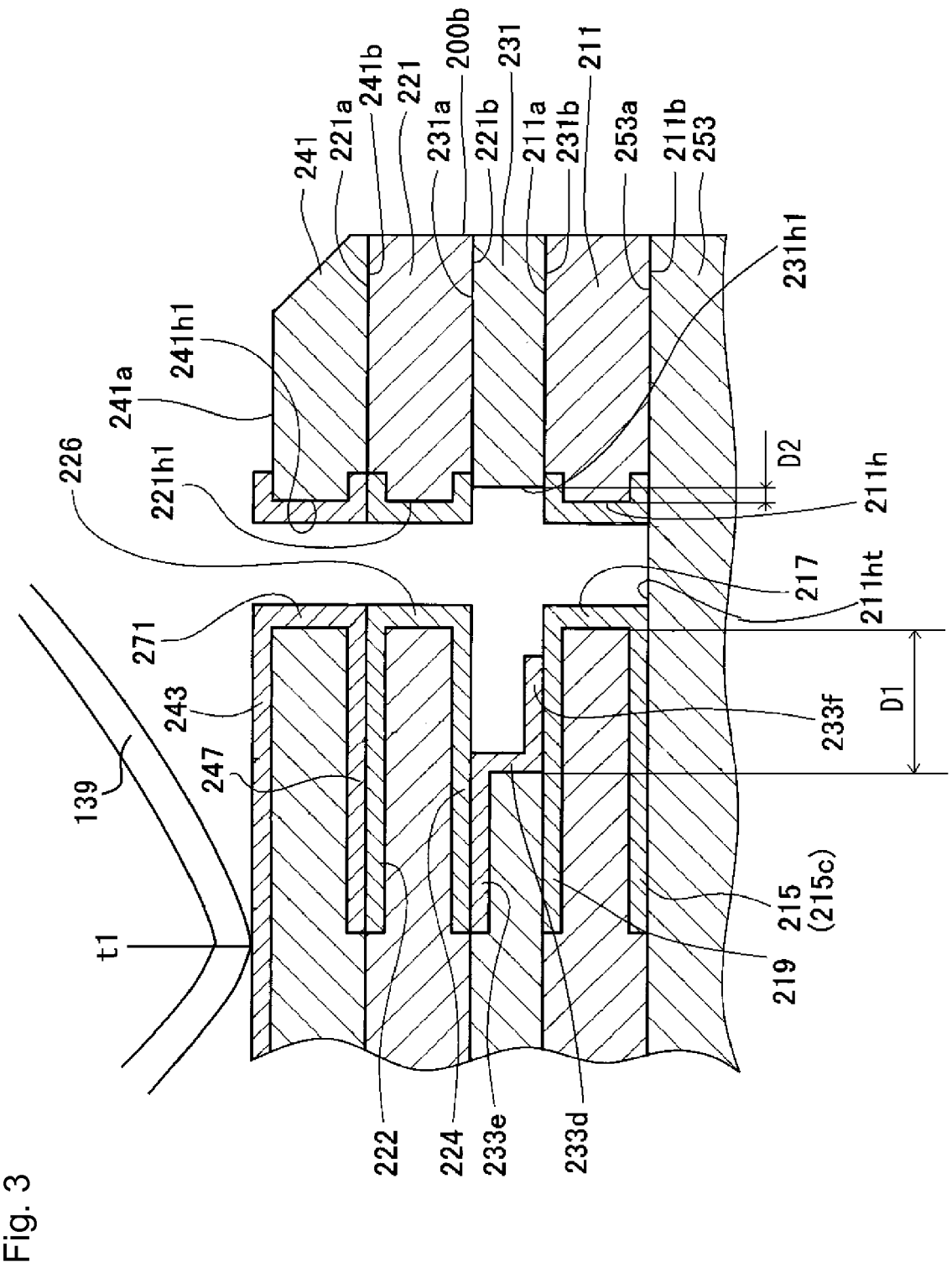
FIG. 3 is an explanatory diagram illustrating the schematic structure of a first conductor of the gas detecting element and vicinity thereof in accordance with the embodiment.

The second through hole 231h1 is connected to the first through hole 211h and the third through hole 221h1 mentioned above, and the cross-sectional area of the second through hole 231h1 is set to be larger than the cross-sectional area of each of the first through hole 211h and the third through hole 221h1 (see FIG. 3). Further, a second through-hole conductor 233d is formed in the second through hole 231h1 at a portion on the leading end side of its inner peripheral surface so as to connect a connecting layer 233e formed on the first surface 231a of the insulating layer 231 and a second connecting layer 233f provided so as to overlap the first connecting layer 219. The base end of the second connecting layer 233f remains on the first connecting layer 219 and does not extend onto the bottom surface 211ht of the first through hole 211.

Figure 4:
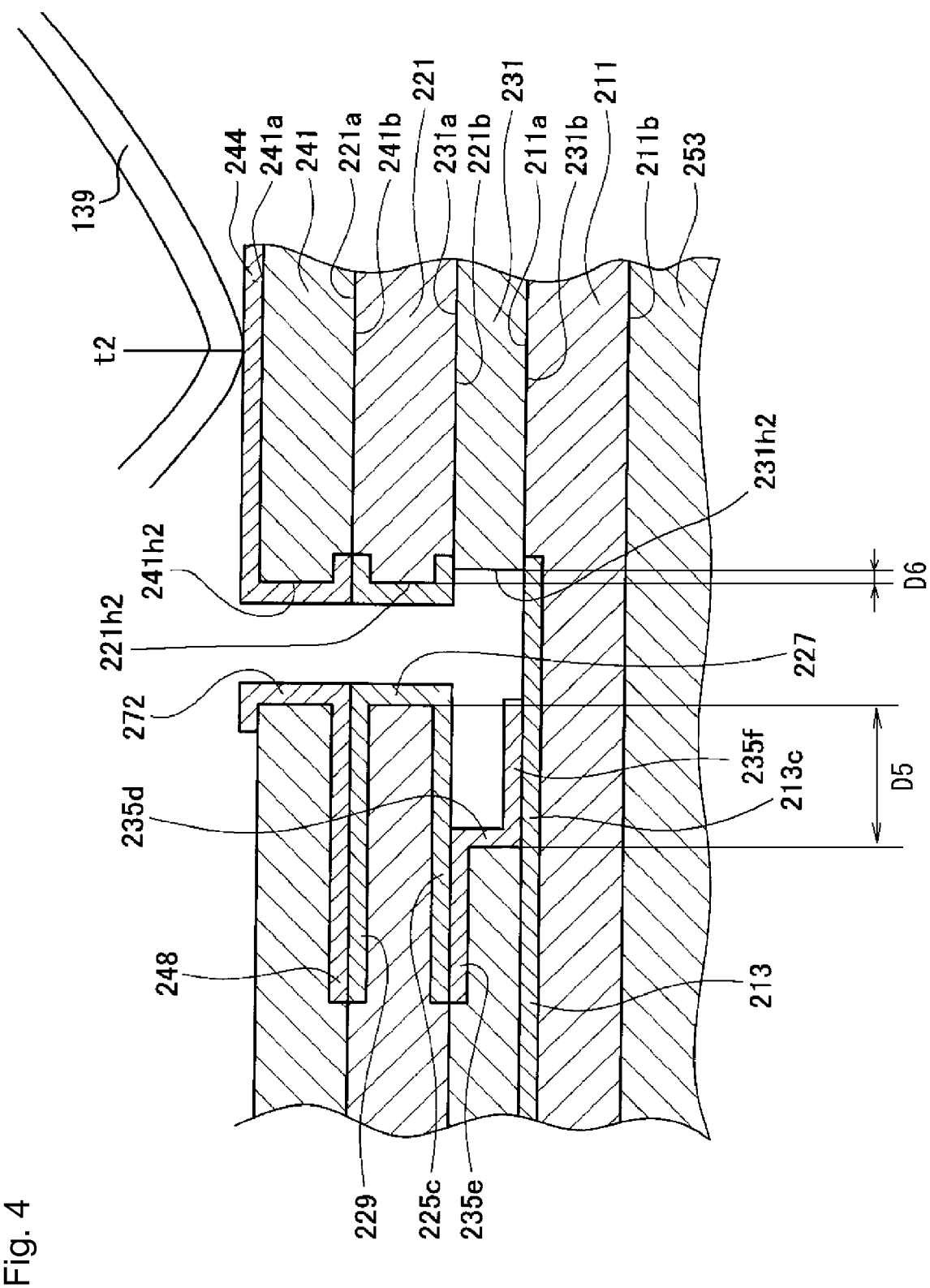
FIG. 4 is an explanatory diagram illustrating the schematic structure of a second conductor of the gas detecting element and vicinity thereof in accordance with the embodiment.

On the other hand, the second through hole 231h2 is connected to the aforementioned third through hole 221h2, and the cross-sectional area of the second through hole 231h2 is set to be larger than the cross-sectional area of the third through hole 221h2 (see FIG. 4). Further, a second through-hole conductor 235d is formed also in the second through hole 231h2 at a portion on the leading end side of its inner peripheral surface so as to connect a connecting layer 235e formed on the first surface 231a of the insulating layer 231 and a second connecting layer 235f provided so as to overlap on the first connecting layer 213c.

Returning to FIG. 2, a description will be given of the protective layer (fourth ceramic layer) 241 which is provided on the first surface 221a side of the second solid electrolyte layer 221 and whose main constituent is alumina. This protective layer 241 includes a porous electrode protecting portion 241e for covering the fourth electrode portion 223a and a reinforcing portion 241d occupying the remaining portion.

Three electrode pads 243, 244 and 245, which are formed of platinum and have a longitudinally extending shape, are formed at predetermined positions on the base end side of a first surface 241a of the protective layer 241 in a juxtaposed manner in the widthwise direction. Meanwhile, three connecting layers 247, 248 and 249, which are formed of platinum and have a longitudinally extending elliptical shape, are also formed at predetermined positions on the base end side of a second surface 241b of the protective layer 241 in a juxtaposed manner. In addition, three fourth through holes 241h1, 241h2 and 241h3 are provided at predetermined positions on the base end side of the protective layer 241.

As shown in FIG. 3, a fourth through-hole conductor 271 is formed on the inner peripheral surface of the fourth through hole 241h1 so as to connect the electrode pad 243 and the connecting layer 247. The connecting layer 247 is overlappingly connected to the aforementioned connecting layer 222. It should be noted that a connection terminal 139 is connected to the connection pad 243 at an abutment position t1.

In addition, as shown in FIG. 4, a fourth through-hole conductor 272 is formed on the inner peripheral surface of the fourth through hole 241h2 so as to connect the electrode pad 244 and the connecting layer 248. The connecting layer 248 is overlappingly connected to the aforementioned connecting layer 229. It should be noted that the connection terminal 139 is connected to the connection pad 244 at an abutment position t2.

Figure 5:
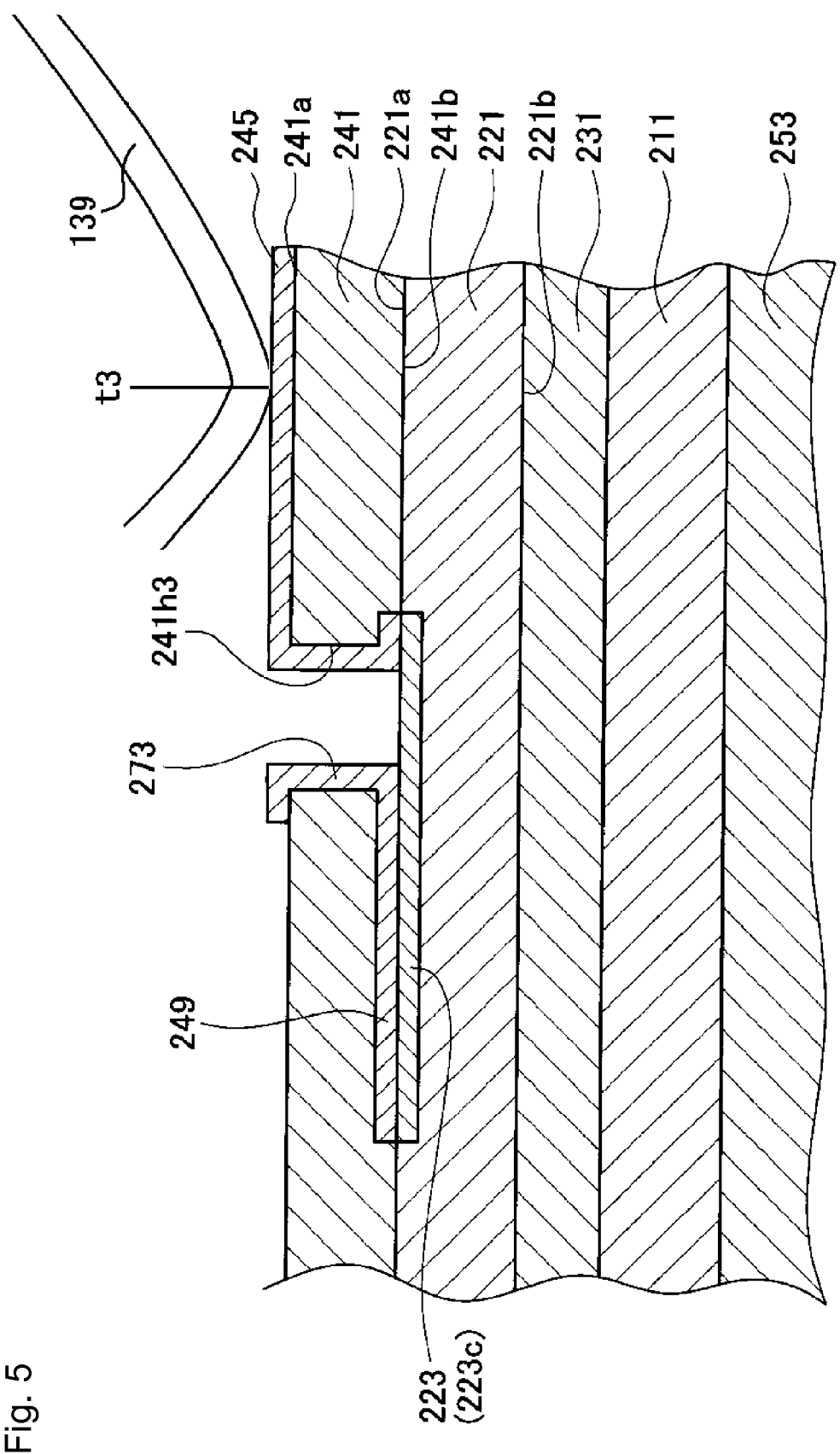
FIG. 5 is an explanatory diagram illustrating the schematic structure of a third conductor of the gas detecting element and vicinity thereof in accordance with the embodiment.

As shown in FIG. 5, a fourth through-hole conductor 273 is formed on the inner peripheral surface of the fourth through hole 241h3 so as to connect the electrode pad 245 and the connecting layer 249. The connecting layer 249 is overlappingly connected to the aforementioned connecting layer 223c. It should be noted that the connection terminal 139 is connected to the connection pad 245 at an abutment position t3.

Figure 9:
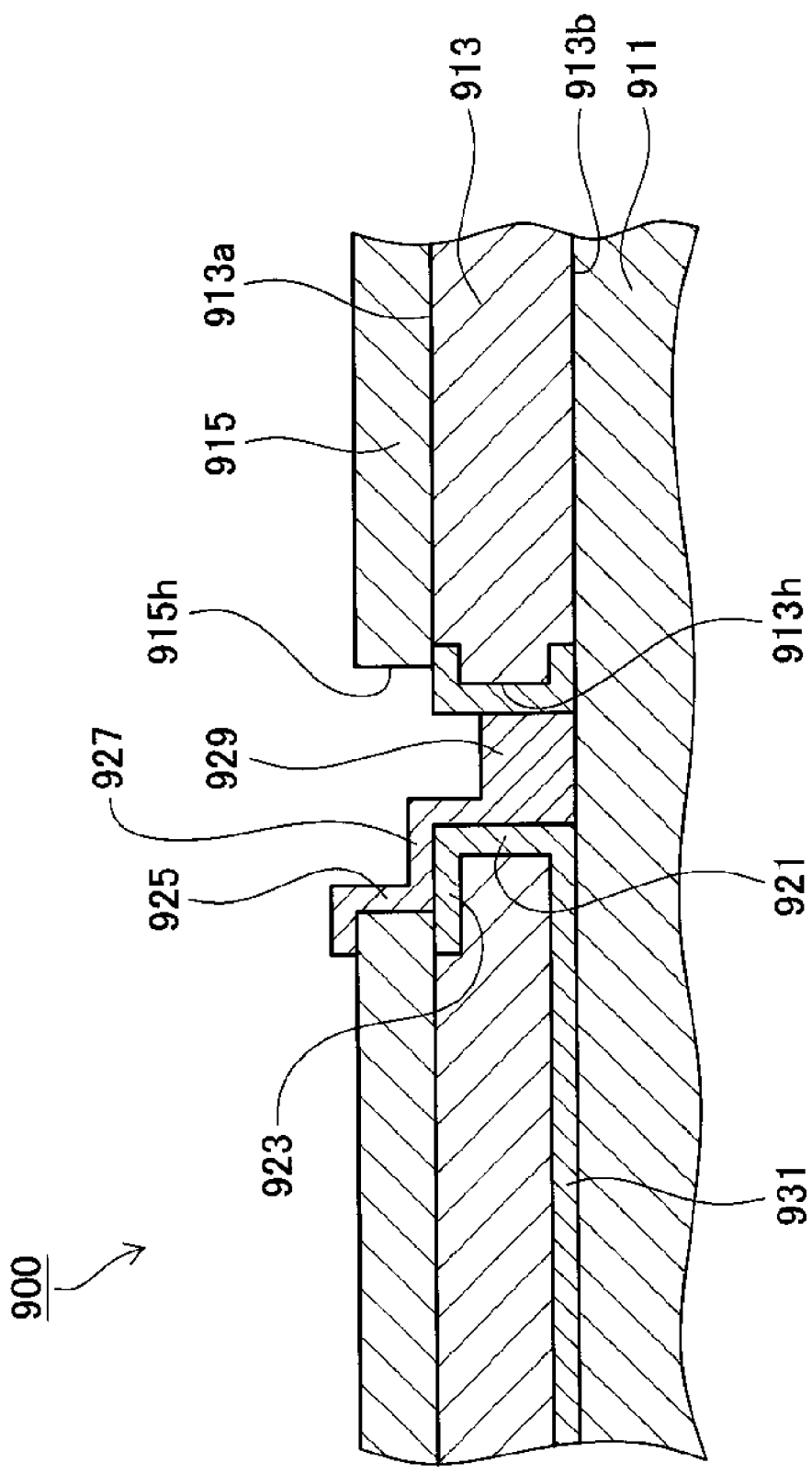
FIG. 9 is an explanatory diagram illustrating the schematic structure of a conductor of a conventional gas detecting element and vicinity thereof.

In the above-described gas detecting element 200, as shown in FIG. 3, the first through-hole conductor 217 and the second through-hole conductor 233d are reliably connected through the first connecting layer 219 and the second connecting layer 233f which are connected in a mutually overlapping manner, so that reliability of electrical connection is high as compared with a case where the first connecting layer 219 and the second connecting layer 233f are absent. Further, in this gas detecting element 200, the second connecting layer 233f is not present on the bottom surface 211ht of the first through hole 211h, i.e., a portion corresponding to the filled through-hole conductor 929 shown in FIG. 9 is not present. In other words, a first surface 253a of the first heater ceramic layer 253 is exposed in the first through hole 211h. For this reason, the gas sensor 100 and gas detecting element 200 are resistant to the occurrence of cracks during sintering or use thereof. Accordingly, the gas detecting element 200 and the gas sensor 100 can exhibit a high degree of electrical reliability.

Further, if the longitudinal distance between a leading end of the first through hole 211h and a leading end of the second through hole 231h1 is taken as D1, and that a longitudinal distance between a base end of the first through hole 211h and a base end of the second through hole 231h1 is D2, the relationship D1>D2>0 is satisfied. As a result, the longitudinal distance between the first through hole 211h or the like and the base end 200b of the sensor detecting element 200 can be made small, preferably not greater than 3 mm. In this embodiment, the longitudinal distance between the first through hole 211h and the base end 200b of the sensor detecting element 200 is approximately 1.5 mm, D1 is approximately 1.2 mm, and D2 is approximately 0.2 mm.

Further, the below-described abutment position t1 between the electrode pad 243 and the connection terminal 139, which abuts against the electrode pad 243 so as to be electrically connected to the electrode pad 243, is offset from the second through hole 231h1 in the longitudinal direction. The mechanical strength of the gas detecting element 200 tends to be small at the portion where the second through hole 231h1 having a relatively large cross-sectional area is provided. However, since the abutment position t1 between the electrode pad 243 and the connection terminal 139 is thus offset from the second through hole 231h1 in the longitudinal direction, even if the connection terminal 139 firmly presses the electrode pad 243, breakage or the like of the gas detecting element 200 is unlikely to occur. In addition, at the time of stacking, a recess can possibly occur in the outer surface 241a of the ceramic detecting element 200 at a portion corresponding to the second through hole 231h1 having a relatively large cross-sectional area. However, since the abutment position t1 of the connection terminal 139 is offset from the second through hole 231h1, the reliability of connection between the connection terminal 139 and the connection pad 243 can be ensured without being affected by the recess.

Further, the second through hole 231h1 is larger than the third through hole 221h1, and the third through-hole conductor 226 formed on the inner peripheral surface of the third through hole 221h1 and the through-hole conductor 233d formed on the inner peripheral surface of the second through hole 221h1 are connected by the connecting layer 233e and the third connecting layer 224. As the opening area of the second through hole 231h1 is made larger than that of the third through hole 221$h$1, the third connecting layer 224 can be formed on the second surface 221$b$ of the second solid electrolyte layer 221 within the second through hole 231$h$1, thereby making it possible to provide the gas detecting element 200 and a gas sensor 100 having high electrical reliability.

In addition, as shown in FIG. 4, the second through hole 231$h$2 is larger than the third through hole 221$h$2, so that the overlapping area of the first connecting layer 213$c$ and the second connecting layer 235$f$ in the second through hole 231$h$2 can be made large. Therefore, it is possible to provide a gas detecting element 200 and a gas sensor 100 having an electrical connection of high reliability between the connection pad 244 and the first connecting layer 213$c$.

Furthermore, the thickness of the insulating layer 231 is smaller than the thickness of the first solid electrolyte layer 211 or the second solid electrolyte layer 221. The second through holes 231$h$1 and 231$h$2 having a relatively large cross-sectional area are formed in the insulating layer 231. Although the mechanical strength of the gas detecting element 200 deteriorates in the vicinity of such second through holes 231$h$1 and 231$h$2, it is possible to suppress the deterioration in mechanical strength by making the thickness of the insulating layer 231 relatively small. It should be noted that, in this embodiment, while the thickness of each of the first solid electrolyte layer 211 and the second solid electrolyte layer 221 is approximately 170 μm, the thickness of the insulating layer 231 is approximately 55 μm, which is less than half the thickness of the solid electrolyte layer.

Furthermore, the below-described abutment position t2 between the electrode pad 244 and the connection terminal 139, which abuts the electrode pad 244 so as to be electrically connected to the electrode pad 244, is located more on the base end side than the third through hole 221$h$2. Meanwhile, if a longitudinal distance between a leading end of the second through hole 231$h$2 and a leading end of the third through hole 221$h$2 is given as D5, and a longitudinal distance between a base end of the second through hole 231$h$ and a base end of the third through hole 221$h$2 is given as D6, the relationship D5>D6>0 is satisfied. In the case where the abutment position t2 is thus located more on the base end side than the third through hole, by making the second through hole 231$h$2 longer toward the leading end side, a structure can be provided in which the abutment position t2 and the second through hole 231$h$2 do not overlap in the thicknesswise direction. As a result, it is possible to prevent breakage of the sensor detecting element 200 due to pressing force of the connection terminal 139, thereby making it possible to improve the mechanical strength of the sensor detecting element. In addition, a recess can possibly occur in the outer surface 241$a$ of the ceramic detecting element 200 at a portion corresponding to the second through hole 231$h$2 having a relatively large cross-sectional area. However, since the abutment position t2 of the connection terminal 139 is offset from the second through hole 231$h$2, the abutment position t2 of the connection terminal 139 is not affected by the recess. Consequently, it is possible to ensure the reliability of connection between the connection terminal 139 and the connection pad 244.

It should be noted that, in this embodiment, D5 is approximately 1.5 mm, and D6 is approximately 0.2 mm.

Next, returning to FIG. 2, a description will be given of the heater portion 251. The heater portion 251 includes the first heater ceramic layer (bottom ceramic layer) 253 and a second heater ceramic layer 255 whose main constituent is alumina; a heating element 257 sandwiched between the first heater ceramic layer 253 and the second heater ceramic layer 255; and a pair of heater-use outer connection pads 261 and 262 provided on the base end side of a second surface 255$b$ of the second heater ceramic layer 255.

The heating element 257 includes a heating portion 257$a$ located on the leading end side; connecting layers 257$c$1 and 257$c$2 located on the base end side; and lead portions 257$b$1 and 257$b$2 for connecting the heating portion 257$a$ and the connecting layers 257$c$1 and 257$c$2, respectively.

Through holes 255$h$1 and 255$h$2 are formed in the second heater ceramic layer 255 so as to penetrate through its first surface 255$a$ and its second surface 255$b$. Conductors 259 and 260 are respectively formed on the inner peripheral surfaces of the through holes 255$h$1 and 255$h$2 so as to electrically connect the connecting layers 257$c$1 and 257$c$2 and the heater-use outer connection pads 261 and 262.

Next, returning to FIG. 1, a description will be given of the construction of the other portions of the gas sensor 100. The metal shell 103 is formed of SUS 430, and has on its outer side an externally threaded portion 105 for installing the gas sensor 100 on the exhaust pipe as well as a hexagonal engaging portion 107 for engaging a tool during the installation. Further, an inner stepped portion 109 protruding inwardly in a radial manner is provided on the inner side of the metal shell 103. This inner stepped portion 109 supports a metal holder 111 for holding the gas detecting element 200. Further, a ceramic holder 113 and a talc filled layer 115 for locating the gas detecting element 200 in position are disposed on the inner side of this metal holder 111 sequentially from the leading end side. This talc filled layer 115 consists of two layers, a first talc filled layer 116 located on the leading end side and a second talc filled layer 117 located on the base end side. An alumina-made sleeve 119 is disposed on the base end side of the second talc filled layer 117. This sleeve 119 is formed into a multi-stage cylindrical shape, and the gas detecting element 200 is inserted in its axial hole 119$h$. A crimped portion 110 located on the base end side of the metal shell 103 is bent inwardly, thereby pressing the sleeve 119 toward the leading end side of the metal shell 103 by means of a stainless steel-made ring member 121.

In addition, the metallic protector 125 for covering a leading end portion 200$s$ of the gas detecting element 200 projecting from the leading end of the metal shell 103 is welded to an outer periphery of the leading end of the metal shell 103. This protector 125 has a dual structure comprising a bottomed cylindrical outer protector 126 located on the outer side and a bottomed cylindrical inner protector 127 located on the inner side. A plurality of gas inlet holes 126$k$ and 127$k$ for respectively introducing the exhaust gases into the interior are provided in the outer protector 126 and the inner protector 127.

Meanwhile, the cylindrical casing 131 made of SUS 430 is welded to the base end side of the metal shell 103. A separator 135 is disposed on the inner side of this casing 131. The separator 135 is fixed to the casing 131 by means of a holding member 137 interposed between the separator 135 and the casing 131. In addition, the plurality of connection terminals 139 for electrically connecting to the gas detecting element 200, as well as a plurality of lead wires 141 whose one ends are electrically connected to these connection terminals 139 and which extend outside the base end side of the gas sensor 100, are disposed on the separator 135. In addition, a cylindrical rubber cap 143 for closing a base end-side opening 131$c$ of the casing 131 is disposed on the base end side of the separator 135. The rubber cap 143 is fixed to the casing 131 by crimping the outer periphery of the casing 131 radially inwardly while being fitted to the casing 131. A plurality of insertion holes 143h are provided in the rubber cap 143, and the aforementioned plurality of lead wires 141 are respectively inserted therein.

Figure 6:
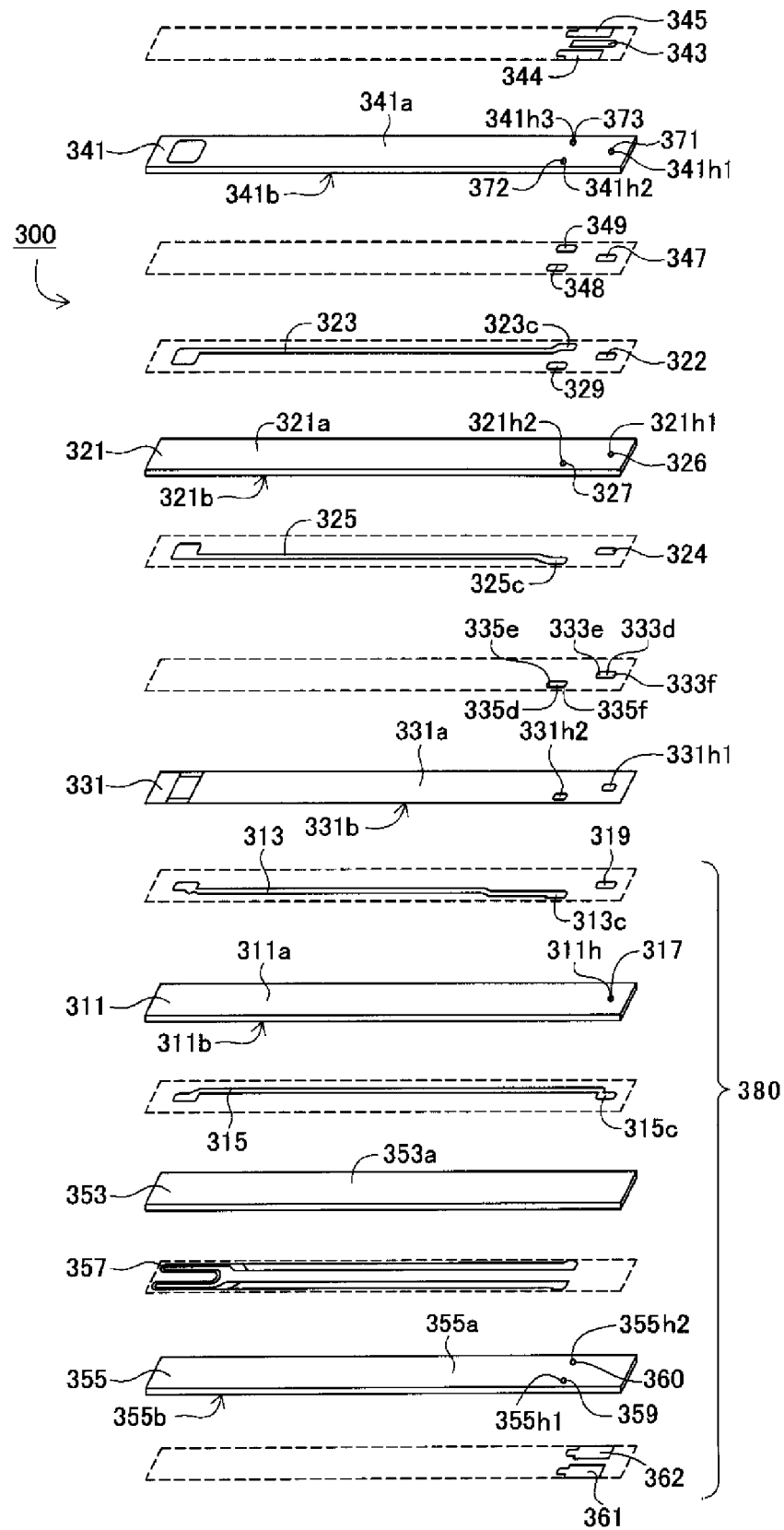
FIG. 6 is an explanatory diagram explaining an outline of a method for manufacturing a gas detecting element in accordance with the embodiment.

Next, a description will be given of a method for manufacturing the gas detecting element 200 (see FIG. 6).

First, the following are respectively prepared by a method such as a known sheet forming method making use of a doctor blade apparatus: a first unsintered heater ceramic layer (bottom ceramic green sheet) 353 which is formed into the first heater ceramic layer 253 after sintering; a second unsintered heater ceramic layer (ceramic green sheet) 355 which is formed into the second heater ceramic layer 255 after sintering; a first unsintered solid electrolyte layer (first ceramic green sheet) 311 which is formed into the first solid electrolyte layer 211 after sintering; a second unsintered solid electrolyte layer (second ceramic green sheet) 321 which is formed into the second solid electrolyte layer 221 after sintering; and an unsintered protective layer (third ceramic green sheet) 341 which is formed into the protective layer 241 after sintering.

Next, unsintered conductors 359 and 360 are formed on the inner peripheral surfaces of through holes 355h1 and 355h2 provided in the second unsintered heater ceramic layer 355 by known screen printing using a conductor paste whose main constituent is platinum. In addition, an unsintered heating element 357 is formed by printing on a first surface 355a of the second unsintered heater ceramic layer 355, and unsintered heater-use outer connection pads 361 and 362 are formed by printing on a second surface 355b thereof.

Subsequently, the first unsintered heater ceramic layer 353 is stacked on the first surface 355a of the second unsintered heater ceramic layer 355 so as to sandwich the unsintered heating element 357.

Figure 7:
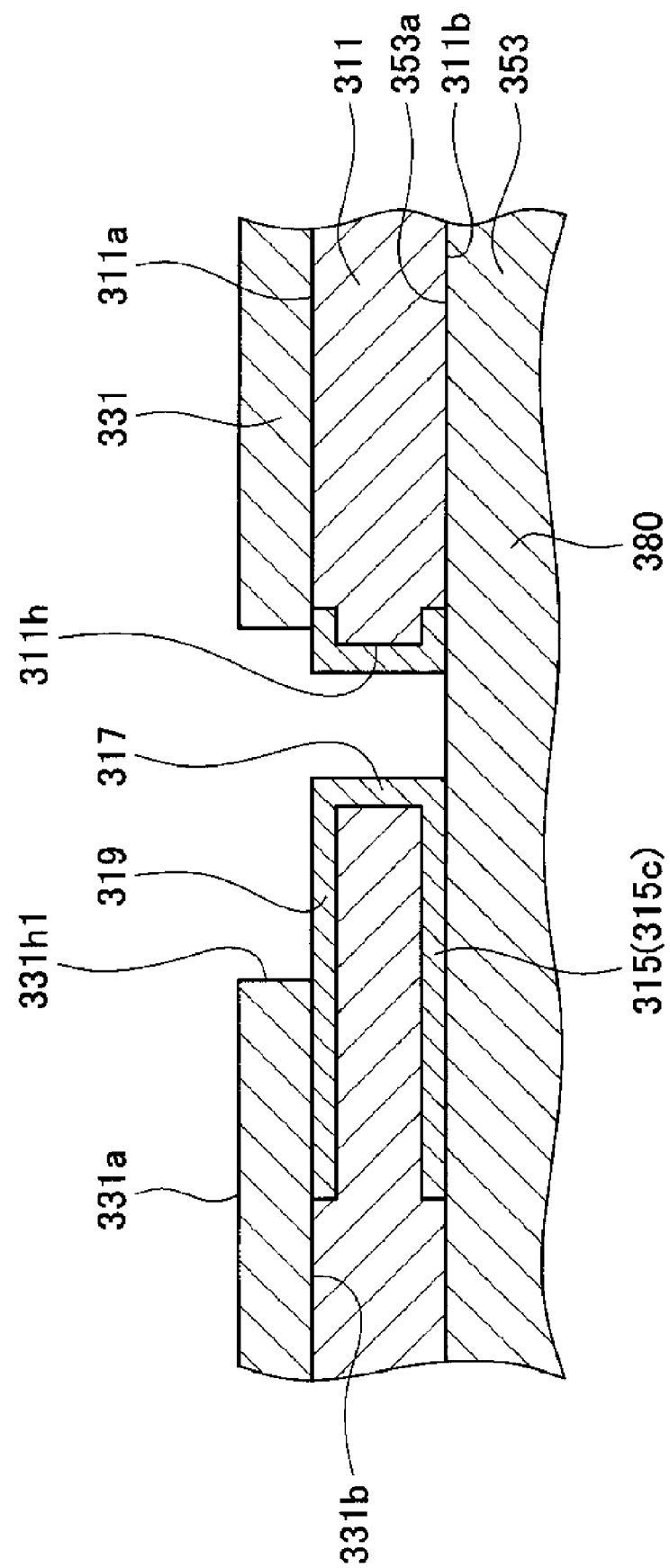
FIG. 7 is an explanatory diagram illustrating a state in which an unsintered insulating layer is formed by printing on a first unsintered solid electrolyte layer in accordance with the embodiment.

In addition, a tubular first unsintered through-hole conductor 317 is formed on the entire inner peripheral surface of a first through hole 311h in the first unsintered solid electrolyte layer 311 by a known screen printing method using a conductor paste whose main constituent is platinum (see also FIG. 7).

In addition, a first unsintered electrode 313 and a first unsintered connecting layer 319 are formed by printing on a first surface 311a of the first unsintered solid electrolyte layer 311. In the first unsintered electrode 313, a first unsintered connecting layer 313c, which is formed into the first connecting layer 213c after sintering, is formed into an elliptical shape extending longitudinally. Further, the first unsintered connecting layer 319 is formed into an elliptical shape which has one end portion connected to the aforementioned first unsintered through-hole conductor 317 and extends toward the longitudinal leading end side.

In addition, a second unsintered electrode 315 is formed by printing on a second surface 311b of the first unsintered solid electrolyte layer 311. In this second unsintered electrode 315, an unsintered connecting layer 315c, which is formed into the connecting layer 215c after sintering, is formed into an elliptical shape which has one end portion connected to the aforementioned first unsintered through-hole conductor 317 and extends toward the longitudinal leading end side.

Subsequently, the second surface 311b of the first unsintered solid electrolyte layer 311 and a first surface 353a of the aforementioned stacked body of the second unsintered heater ceramic layer 355 and the first unsintered heater ceramic layer 353 are put together so as to sandwich the second unsintered electrode 315, thereby forming a stacked intermediate body 380 (see also FIG. 7). The first unsintered heater ceramic layer 353 is exposed in the first through hole 311h.

Next, an unsintered insulating layer 331 having a bottom surface 331b is formed by printing (by a known screen printing method) on the first surface 311a of the first unsintered solid electrolyte layer 311a conductor paste whose main constituent is alumina (see also FIG. 7). This unsintered insulating layer 331 has a thickness of 65 μm. In addition, elliptical second through holes 331h1 and 331h2 having a larger cross-sectional area than the aforementioned first through hole 311h are respectively formed in the unsintered insulating layer 331.

Next, a conductor paste DP whose main constituent is platinum is applied to an area covering the first surface 331a of the unsintered insulating layer 331, a portion of the inner peripheral surface of the second through hole 331h1, and the top of the first connecting layer 319 by a known screen printing method, to thereby continuously form an unsintered connecting layer 333e, a second unsintered through-hole conductor 333d, and a second unsintered connecting layer 333f. This second unsintered connecting layer 333f is formed such that its one end portion is connected to the aforementioned second unsintered through-hole conductor 333d, and its other end does not reach the interior of the first through hole but is located on top of the first unsintered connecting layer 319 (see FIG. 8).

In addition, an unsintered connecting layer 335e is formed by printing on the first surface 331a, a second unsintered through-hole conductor 335d is formed by printing on a portion of the inner peripheral surface of the through hole 331h2 of the unsintered insulating layer 331, and a second unsintered connecting layer 335f is formed by printing on the unsintered connecting layer 313c exposed in the through hole 331h2.

In addition, second unsintered through-hole conductors 326 and 327 are respectively formed on the inner peripheral surfaces of through holes 321h1 and 321h2 of the second unsintered solid electrolyte layer 321 by a known screen printing method using a conductor paste whose main constituent is platinum. Further, a third unsintered electrode 323, an unsintered connecting layer 322 and an unsintered connecting layer 329 are formed by printing on a first surface 321a of the second unsintered solid electrolyte layer 321. Further, a fourth unsintered electrode 325 and a third unsintered connecting layer 324 are formed by printing on a second surface 321b of the second unsintered solid electrolyte layer 321. Subsequently, this second unsintered solid electrolyte layer 321 is stacked on a first surface 331a of the unsintered insulating layer 331.

In addition, fourth unsintered through-hole conductors 371, 372 and 373 are respectively formed on the inner peripheral surfaces of through holes 341h1, 341h2 and 341h3 of the unsintered protective layer 341 by a known screen printing method using a conductor paste whose main constituent is platinum. Further, unsintered electrode pads 343, 344 and 345 for respectively connecting to the fourth unsintered through-hole conductors 371, 372 and 373 are formed by printing on a first surface 341a of the unsintered protective layer 341. Meanwhile, unsintered connecting layers 347, 348 and 349 for respectively connecting to the fourth unsintered through-hole conductors 371, 372 and 373 are formed by printing on a second surface 341b of the unsintered protective layer 341.

Subsequently, this unsintered protective layer 341 is stacked on the first surface 321a of the second unsintered solid electrolyte layer 321.

Thus, an unsintered ceramic stacked body 300 is formed.

Subsequently, this unsintered ceramic stacked body 300 is sintered by a known method. As a result, the above-described gas detecting element 200 is formed.

As described above, in this embodiment, not only the first unsintered through-hole conductor 317 but also the first unsintered connecting layer 319 which is connected thereto is formed on the first unsintered solid electrolyte layer 311. In addition, not only the second unsintered through-hole conductor 333 but also the second unsintered connecting layer 333f which is connected thereto and overlaps the first unsintered connecting layer 319 is formed on the unsintered insulating layer 331. Further, the first through-hole conductor 217, the second through-hole conductor 233d, the first connecting layer 219 and the second connecting layer 233f are formed by sintering. By so forming, the first through-hole conductor 217 and the second through-hole conductor 233d can be reliably connected by means of the first connecting layer 219 and the second connecting layer 233f which are connected together in an overlapping manner. Therefore, the degree of reliability of electrical connection in the thicknesswise direction is high.

Figure 8:
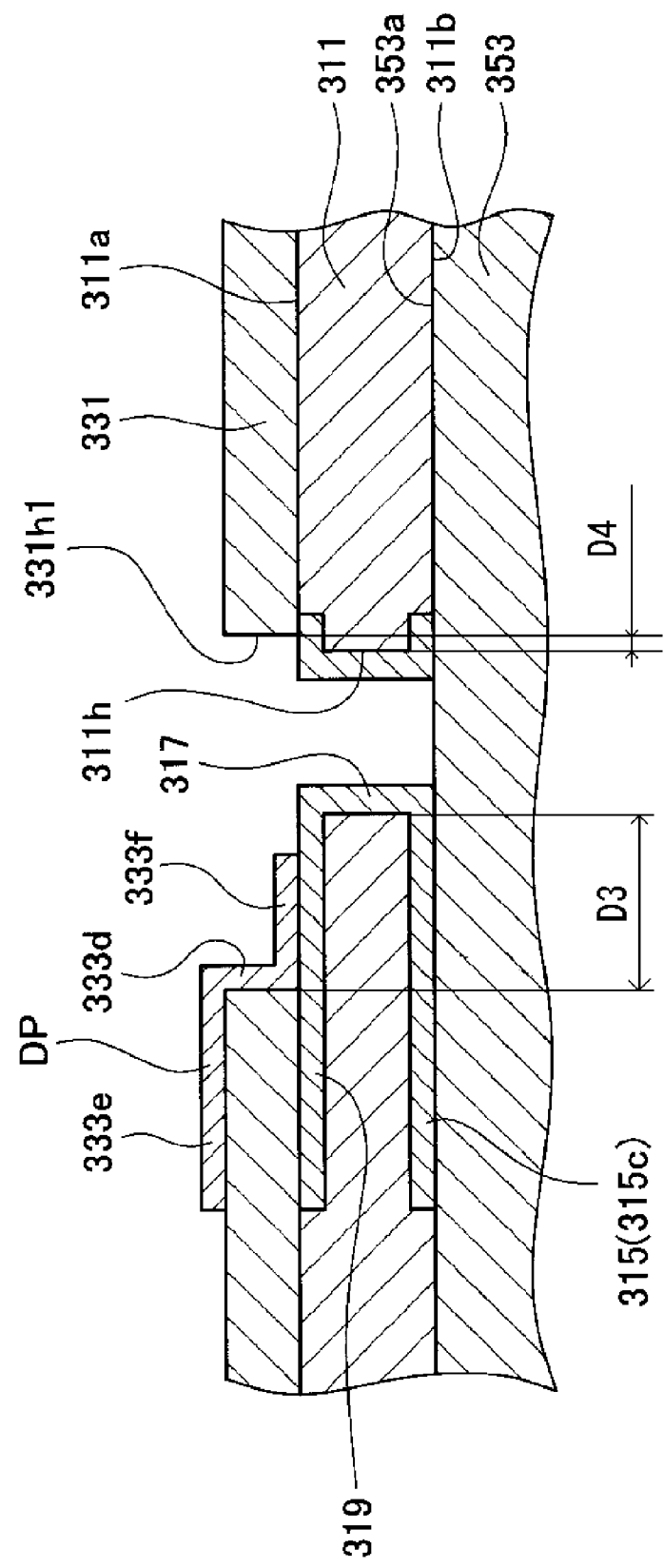
FIG. 8 is an explanatory diagram illustrating a state in which a conductor paste is printed on an unsintered insulating layer in accordance with the embodiment.

Furthermore, in this embodiment, when the second unsintered through-hole conductor 333d and the second unsintered connecting layer 333f are formed by printing, the unsintered first heater ceramic layer 353 is exposed in the first through hole 311h, and the conductor paste is not applied to the top of the first surface 353a of the unsintered first heater ceramic layer 353 (see FIG. 8). Moreover, the conductor paste is originally absent from the first surface 353a of the unsintered first heater ceramic layer 353. For this reason, it is possible to prevent or suppress the occurrence of cracking during sintering. Accordingly, it is possible to manufacture a gas detecting element 200 and gas sensor 100 having high electrical reliability.

In addition, in this embodiment, the unsintered insulating layer 331 is formed on the first unsintered solid electrolyte layer 311 by printing an insulation paste. Consequently, the second unsintered through-hole conductor 333d and the second unsintered connecting layer 333f cannot be printed in advance on the unsintered insulating layer 331 such as in the case where the unsintered insulating layer 331 is formed by stacking a ceramic green sheet. In particular, in this embodiment, since the thin unsintered insulating layer 331 having a thickness of not greater than 100 μm is formed, it is difficult to form the unsintered insulating layer 331 by a method in which a ceramic green sheet is stacked. However, even in such a case, by applying the manufacturing method described in this embodiment, the unsintered ceramic stacked body 300 can be easily formed by exposing the unsintered substrate 353 within the first through hole 311h. Accordingly, it is possible to prevent or suppress the occurrence of cracking during sintering.

Furthermore, if the longitudinal distance between a leading end of the first through hole 311h and a leading end of the second through hole 331h1 is given as D3, and the a longitudinal distance between a base end of the first through hole 311h and a base end of the second through hole 331h1 is D4, the relationship D3>D4>0 holds. As a result, it is possible to suppress the electrode pad 243 and the second through hole 231h1, which are formed on the base end side of the gas detecting element 200, from overlapping in the axial direction, thereby making it possible to provide a gas detecting element 200 and gas sensor 100 having high electrical connection reliability after sintering.

Further, the thickness of the unsintered insulating layer 331 having the through hole 331h with a relatively large cross-sectional area is smaller than the thickness of the first unsintered solid electrolyte layer 311. Although there is a possibility of impairing the mechanical strength of the stacked body 300 due to the presence of the through hole 331h, by making the thickness of the unsintered insulating layer 331 relatively small, it is possible to suppress such a decline of the mechanical strength. The thickness of the unsintered insulating layer 331 is preferably set to be not more than half the thickness of the first unsintered solid electrolyte layer 311.

Although the present invention has been described above in accordance with the above embodiment, the invention is not limited thereto. Namely, the invention may be modified to implement the same, as needed, within the scope of the claims appended hereto.

For example, in the above-described embodiment, the connecting layers 219, 233e, 224, 222, 247, 235e, 225c, 229, 248 and 249 are respectively formed so as to extend toward the longitudinal leading end side of the gas detecting element 200. However, the form of these connecting layers is not so limited, and the connecting layers may be formed, for instance, so as to extend toward the longitudinal base end side, depending on the position of the through hole formed in the gas detecting element. Furthermore, the connecting layers may be formed so as to extend in the widthwise direction of the gas detecting element, in a case where there is a sufficient space in the widthwise direction of the gas detecting element.

Furthermore, although, in the foregoing embodiment, a total of six layers, including the substrates (the first heater ceramic layer 253 and the second heater ceramic layer 255), the insulating layers (the insulating layer 231 and the protective layer 241), and the solid electrolyte layers (the first solid electrolyte layer 211 and the second solid electrolyte layer 221), are stacked, the invention is not limited thereto, and it suffices if a total of at least two or more layers are stacked among the substrates, the insulating layers and the solid electrolyte layers.

Although the invention has been described above in relation to preferred embodiments and modifications thereof, it will be understood by those skilled in the art that other variations and modifications can be effected in these preferred embodiments without departing from the scope and spirit of the invention.

This application is based on Japanese Patent Application JP 2006-195783, filed Jul. 18, 2006, the entire content of which is hereby incorporated by reference, the same as if set forth at length.

What is claimed is:

1. A gas sensor comprising a gas detecting element extending in a longitudinal direction and in which a plurality of ceramic layers are stacked, and wherein a detecting portion is provided at a leading end side of the gas detecting element, the gas detecting element comprising:
a first ceramic layer having a first surface and a second surface and having a first through hole penetrating therethrough;
a second ceramic layer stacked on a side of the first surface of the first ceramic layer and having a second through hole connected to the first through hole, the second through hole having an opening area larger than that of the first through hole;
a bottom ceramic layer which is stacked on a side of the second surface of the first ceramic layer to close one end of the first through hole;
a first through-hole conductor provided on an inner peripheral surface of the first through hole;
a first connecting layer provided on the first surface of the first ceramic layer and connected to the first through-hole conductor;
a second through-hole conductor provided on an inner peripheral surface of the second through hole; and a second connecting layer having one end disposed on the first connecting layer and another end connected to the second through-hole conductor, wherein the one end of the second connecting layer does not reach the first through hole such that the second connecting layer is connected to only a part of the first connecting layer.

2. The gas sensor as claimed in claim 1, wherein a surface of the bottom ceramic layer is exposed in the first through hole.

3. The gas sensor as claimed in claim 1, wherein a relationship D1>D2>0 is satisfied, where D1 represents a longitudinal distance between a leading end of the first through hole and a leading end of the second through hole, and D2 represents a longitudinal distance between a base end of the first through hole and a base end of the second through hole.

4. The gas sensor as claimed in claim 3, wherein the gas detecting element further comprises:

an electrode pad electrically connected to the second through-hole conductor and provided on an outer surface of the gas detecting element; and a connection terminal abutting the electrode pad so as to be electrically connected to the electrode pad, wherein the second through hole and a position of abutment between the connection terminal and the electrode pad are offset in the longitudinal direction.

5. The gas sensor as claimed in claim 1, wherein a thickness of the second ceramic layer is smaller than a thickness of the first ceramic layer.

6. The gas sensor as claimed in claim 1, wherein the gas detecting element further comprises:

a third ceramic layer having a first surface and a second surface and having a third through hole penetrating therethrough;

a third through-hole conductor provided on an inner peripheral surface of the third through hole; and a third connecting layer provided on the second surface of the third ceramic layer and connecting the third through-hole conductor and the second through-hole conductor, wherein the second ceramic layer is stacked on the side of the second surface of the third ceramic layer, and the second through hole is connected to the third through hole and has an opening area larger than that of the third through hole.

7. A method for manufacturing a gas sensor including, a gas detecting element extending in a longitudinal direction and in which a plurality of ceramic layers are stacked, and wherein a detecting portion is provided at a leading end side of the gas detecting element, the gas detecting element comprising:

a first ceramic layer having a first surface and a second surface and having a first through hole penetrating therethrough;

a second ceramic layer stacked on a side of the first surface of the first ceramic layer and having a second through hole connected to the first through hole, the second through hole having an opening area larger than that of the first through hole;

a bottom ceramic layer which is stacked on a side of the second surface of the first ceramic layer to close one end of the first through hole;

a first through-hole conductor provided on an inner peripheral surface of the first through hole;

a first connecting layer provided on the first surface of the first ceramic layer and connected to the first through-hole conductor;

a second through-hole conductor provided on an inner peripheral surface of the second through hole; and a second connecting layer having one end disposed on the first connecting layer and another end connected to the second through-hole conductor, wherein the one end of the second connecting layer does not reach the first through hole such that the second connecting layer is connected to only a part of the first connecting layer, said method comprising:

in a first ceramic green sheet having a first surface and a second surface and having a first through hole penetrating therethrough, forming a first unsintered through-hole conductor on an inner peripheral surface of the first through hole and forming on the first surface a first unsintered connecting layer for connecting to the first unsintered through-hole conductor;

stacking a bottom ceramic green sheet on a side of the second surface of the first ceramic green sheet so as to close one end of the first through hole;

stacking on a side of the first surface of the first ceramic green sheet a second unsintered ceramic layer having a second through hole formed in a position corresponding to the first through hole, the second through hole having a cross-sectional area larger than that of the first through hole;

printing a conductor paste on an inner peripheral surface of the second through hole and the first surface of the first ceramic sheet exposed in the second through hole, so as to form a second unsintered through-hole conductor provided on the inner peripheral surface of the second through hole and a second unsintered connecting layer having one end connected to the second unsintered through-hole conductor and another end formed on the first connecting layer; and sintering a completed stacked body.

8. The method as claimed in claim 7, wherein a surface of the bottom ceramic green sheet is exposed in the first through hole.

9. The method as claimed in claim 7, wherein a relationship D3>D4>0 is satisfied, where D3 represents a longitudinal distance between a leading end of the first through hole and a leading end of the second through, and D4 represents a longitudinal distance between a base end of the first through hole and a base end of the fourth through hole.

10. The method as claimed in claim 7, wherein a thickness of the second unsintered ceramic layer is smaller than a thickness of the first ceramic green sheet.

11. The method as claimed in claim 7, wherein the second unsintered ceramic layer is formed by printing an insulation paste.

12. The method as claimed in claim 11, wherein the second unsintered ceramic layer is formed to have a thickness of not greater than 100 μm.

13. A gas sensor comprising a gas detecting element extending in a longitudinal direction and in which a plurality of ceramic layers are stacked, and wherein a detecting portion is provided at a leading end side of the gas detecting element, the gas detecting element comprising:

a first ceramic layer having a first surface and a second surface;

a third ceramic layer having a first surface and a second surface and having a third through hole penetrating therethrough;

a second ceramic layer provided between the first surface of the first ceramic layer and the second surface of the third ceramic layer and having a second through hole connected to the third through hole, the second through hole having an opening area larger than that of the third through hole;
a first connecting layer provided on the first surface of the first ceramic layer and exposed in the second through hole;
a second through-hole conductor provided on an inner peripheral surface of the second through hole;
a second connecting layer having one end disposed on the first connecting layer and another end connected to the second through-hole conductor;
a third through-hole conductor provided on an inner peripheral surface of the third through hole; and
a third connecting layer provided on the second surface of the third ceramic layer and connecting the second through-hole conductor and the third through-hole conductor.

14. The gas sensor as claimed in claim 13, wherein the gas detecting element further comprises:
an electrode pad electrically connected to the second through-hole conductor and provided on an outer surface of the gas detecting element; and
a connection terminal abutting the electrode pad at a position located closer to a longitudinal base end side than the third through hole so as to be electrically connected to the electrode pad, and
wherein a relationship $D5>D6>0$ is satisfied, where $D5$ represents a longitudinal distance between a leading end of the second through hole and a leading end of the third through hole, and $D6$ represents a longitudinal distance between a base end of the second through hole and a base end of the third through hole.

* * * * *